US012643900B2

(12) United States Patent
Qin et al.

(10) Patent No.: US 12,643,900 B2
(45) Date of Patent: Jun. 2, 2026

(54) METHOD FOR PREPARING FORODESINE

(71) Applicants: SICHUAN UNIVERSITY, Chengdu (CN); ACADEMY OF MILITARY MEDICAL SCIENCES, Beijing (CN)

(72) Inventors: Yong Qin, Chengdu (CN); Wu Zhong, Beijing (CN); Fei Xue, Chengdu (CN); Minjie Zhang, Chengdu (CN); Shiyong Fan, Beijing (CN); Zhibing Zheng, Beijing (CN); Song Li, Beijing (CN)

(73) Assignees: SICHUAN UNIVERSITY, Chengdu (CN); ACADEMY OF MILITARY MEDICAL SCIENCES, Beijing (CN)

( * ) Notice: Subject to any disclaimer, the term of this patent is extended or adjusted under 35 U.S.C. 154(b) by 657 days.

(21) Appl. No.: 18/018,012

(22) PCT Filed: Jul. 22, 2021

(86) PCT No.: PCT/CN2021/107836

§ 371 (c)(1),
(2) Date: Jan. 25, 2023

(87) PCT Pub. No.: WO2022/022376

PCT Pub. Date: Feb. 3, 2022

(65) Prior Publication Data

US 2023/0271970 A1 Aug. 31, 2023

(30) Foreign Application Priority Data

Jul. 30, 2020 (CN) ......................... 202010752502.5

(51) Int. Cl.
*C07D 487/04* (2006.01)

(52) U.S. Cl.
CPC ................................. *C07D 487/04* (2013.01)

(58) Field of Classification Search
None
See application file for complete search history.

(56) References Cited

U.S. PATENT DOCUMENTS

2018/0258091 A1 9/2018 Bass et al.

FOREIGN PATENT DOCUMENTS

CN 101153040 A 4/2008
CN 101475491 A 8/2009
(Continued)

OTHER PUBLICATIONS

Greene and Wuts, "Greene's Protective Groups in Organic Synthesis" John Wiley & Sons, Inc. 2007, DOI:10.1002/0470053488. Published Apr. 10, 2006. Select pages from Proctetion for the Hydroxyl Group. (Year: 2006).*
(Continued)

*Primary Examiner* — Jennifer A Berrios
*Assistant Examiner* — Sophia Reilly
(74) *Attorney, Agent, or Firm* — Leason Ellis LLP; James F. Haley, Jr.; Kendra V. Johnson

(57) ABSTRACT

The present invention relates to the technical field of chemical drug synthesis, and specifically relates to a method for preparing a compound as shown in formula I, comprising: treating the compound as shown in formula VII with an acid to generate the compound as shown in formula I. The method has few synthetic process steps, raw materials which is stable and is easy to prepare, a reaction process which is
(Continued)

1
$^1$H NMR(400 MHz, $d_6$-DMSO)

easy to control, and a high overall yield and purity, and is suitable for industrial preparation.

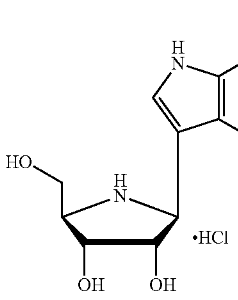

I

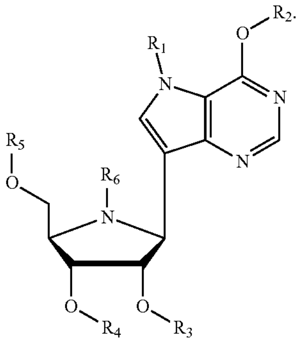

VII

19 Claims, 3 Drawing Sheets

(56) References Cited

FOREIGN PATENT DOCUMENTS

| | | | | | |
|---|---|---|---|---|---|
| CN | 101693708 | A | | 4/2014 | |
| CN | 107108639 | A | | 8/2017 | |
| CN | 111704619 | A | | 9/2020 | |
| JP | 2002-542170 | A | | 12/2002 | |
| JP | 2015-514772 | A | | 5/2015 | |
| WO | 2000/061783 | A2 | | 10/2000 | |
| WO | 2013/158746 | A1 | | 10/2013 | |
| WO | 2014078778 | A2 | | 5/2014 | |
| WO | WO-2016110527 | A1 | * | 7/2016 | ........... A61K 31/519 |

OTHER PUBLICATIONS

Greene and Wuts, "Greene's Protective Groups in Organic Synthesis" John Wiley & Sons, Inc. 2007, DOI:10.1002/0470053488. Published Apr. 10, 2006. Select Pages from Protection for the Amino Group. (Year: 2006).*

Moore et al. "Universal characteristics of chemical synthesis and property optimization" Chem Sci 2011, 2, 417-424. DOI: 10.1039/cOsc00425a (Year: 2011).*

Kamath et al., "Synthesis of analogs of forodesine HCI, a human purine nucleoside phosphorylase inhibitor—Part I", Bioorganic & Medicinal Chemistry Letters, 19(10):2624-2626 (2009).

Xu, "Synthetic organic chemistry and modern technology", Northwestern Polytechnical University Press, Dec. 1997, pp. 106-111 (with English Translation).

Greene T.W. et al., "Protection for the Hydroxyl Group, Including 1,2- And 1,3-Diols", Protective Groups in Organic Synthesis, Jan. 1, 1991, XP002918777, 78 Pages.

Holzapfel C.W., "Synthesis and Reactions of Chiral Cyclic Nitrones Derived from D-Ribose", Heterocycles, vol. 48, No. 7, 1998, p. 1337-1342.

Tsou E-L., et al., "A convenient approach toward the synthesis of enantiopure isomers of DMDP and ADMDP" Tetrahedon, vol. 65, 2009, pp. 93-100.

* cited by examiner

1

$^{13}C$ NMR(100 MHz, $d_6$-DMSO)

Signal 1: DAD1 A, Sig=254,4 Ref=360,100

| Peak # | RetTime [min] | Type | Width [min] | Area [mAU*s] | Height [mAU] | Area % |
|---|---|---|---|---|---|---|
| 1 | 7.383 | BB | 0.2606 | 19.30883 | 1.03992 | 0.0130 |
| 2 | 9.307 | BB | 0.2463 | 105.91992 | 6.42738 | 0.0714 |
| 3 | 10.550 | BB | 0.7339 | 1.48284e5 | 3111.81201 | 99.9156 |

1260-DAD 10/8/2019 7:50:34 PM 系統 Page 1 of 2

Data File D:\Data\AXF191008-BCX1777\2019-10-08-2.D
Sample Name: AXF191008-BCX1777

| Peak # | RetTime [min] | Type | Width [min] | Area [mAU*s] | Height [mAU] | Area % |
|---|---|---|---|---|---|---|
| Totals : | | | | 1.48409e5 | 3119.27931 | |

METHOD FOR PREPARING FORODESINE

CROSS-REFERENCE TO RELATED APPLICATIONS

This application is a national stage application under 35 U.S.C. § 371 of International Application No. PCT/CN2021/107836, filed Jul. 22, 2021, which claims the benefit of and priority from Chinese Application No. 202010752502.5, filed on Jul. 30, 2020. The contents and disclosure of each of the foregoing applications are incorporated herein by reference in their entireties.

TECHNICAL FIELD

The present invention belongs to the technical field of chemical drug synthesis, and relates to a method for preparing Forodesine.

BACKGROUND ART

Forodesine, also known as BCX-1777, is a purine nucleoside phosphorylase (PNP) inhibitor. Forodesine was approved as an orphan drug in the United States in 2004 for the treatment of T-cell non-Hodgkin lymphoma and chronic myeloid leukemia. It was approved as an orphan drug in the European Union in 2006, 2007 and 2010 respectively for the treatment of acute lymphocytic leukemia, cutaneous T-cell lymphoma, and chronic lymphocytic leukemia. In 2017, Forodesine was approved in Japan for the treatment of relapsed/refractory peripheral T-cell lymphoma.

The first-line treatment options for peripheral T-cell lymphoma are mainly multidrug chemotherapy (including cyclophosphamide, doxorubicin, vincristine, and prednisone) and brentuximab vedotin (Adcetris). For the treatment of relapsed/refractory peripheral T-cell lymphoma, the options are limited and the effect is not satisfactory. Currently, three histone deacetylation inhibitors, namely Chidamide, Romidepsin and Belinostat, are commonly used, in which Chidamide is only approved in China, and Romidepsin and Belinostat are only approved in the United States. As a novel nucleoside metabolic inhibitor, Forodesine can effectively inhibit T-cell function and is a valuable drug for the treatment of relapsed/refractory peripheral T-cell lymphoma.

In addition, Forodesine is also a key intermediate necessary for the synthesis of broad-spectrum antiviral drug Galidesivir (BCX-4430), which is indispensable in the synthesis of BCX-4430.

However, the industrial preparation of Forodesine is very difficult. According to literature reports (Nature, 2014, 508, 402-405), the currently used industrial preparation scheme is as follows.

In this scheme, secondary amine (8) is used as starting material and is chlorinated and dechlorinated to obtain imine (10). Under the action of n-butyllithium, bromopurine derivative (2) is lithiated, and then undergoes an addition reaction with imine (10), and the obtained secondary amine intermediate is protected with Boc to obtain intermediate (11), which is then hydrogenated to remove BOM protecting group, and heated with concentrated hydrochloric acid to remove other protecting groups to obtain Forodesine hydrochloride, which is finally purified through ion exchange resin and recrystallization to obtain Forodesine.

In this preparation scheme, the preparation of the raw material secondary amine (8) is complicated and expensive, and the cost of raw materials is high; the imine formed by the two-step transformation is low in yield, unstable, and not easy to store; the removal of BOM protecting group of heterocycle requires hydrogenation, which requires special equipment and has certain risks, and all these factors are not conducive to industrial-scale production.

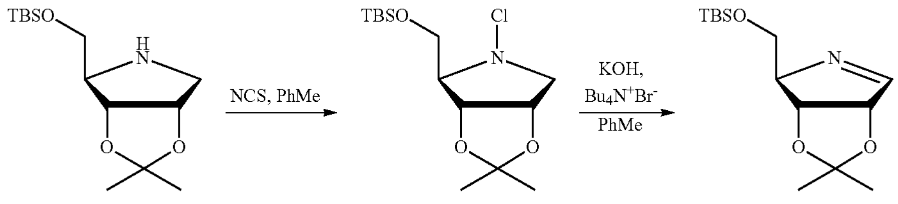

8 9 10

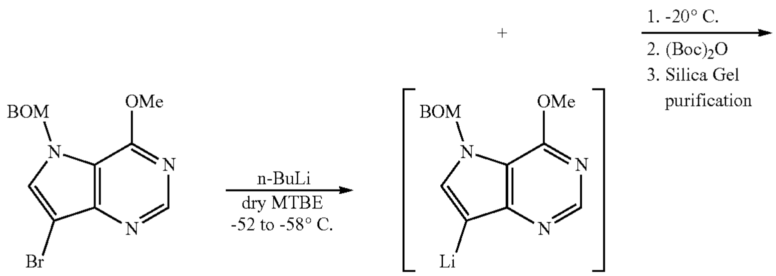

2 3

-continued

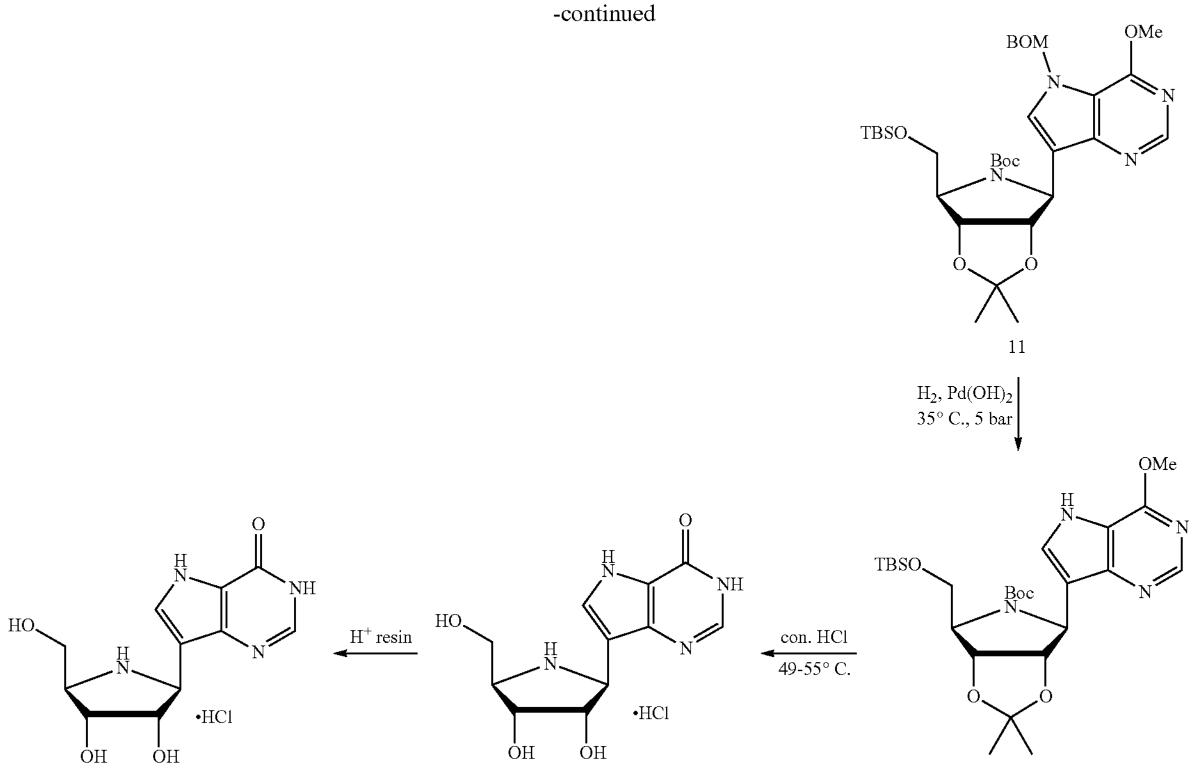

11, 12, forodesine hydrochloride (1), 1

Patent application US20180258091A1 discloses a new process as shown below to improve the above scheme. In this scheme, n-hexyllithium is used instead of n-butyllithium, and the bromopurine derivative (2) is lithiated at −15° C., which reduces the requirement for low temperature of the reaction equipment; in addition, the method of removing the BOM protecting group through hydrogenation is changed to removing the BOM protecting group through concentrated hydrochloric acid, which avoids the dangerous high pressure hydrogenation conditions.

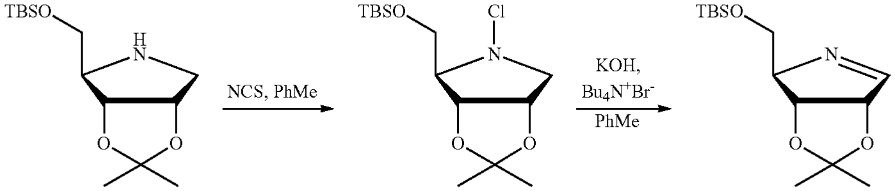

8 9 10

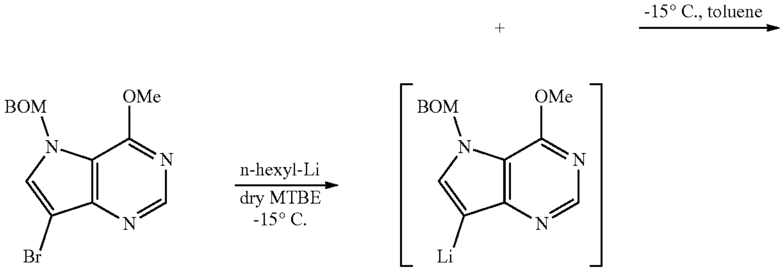

2 3

-continued

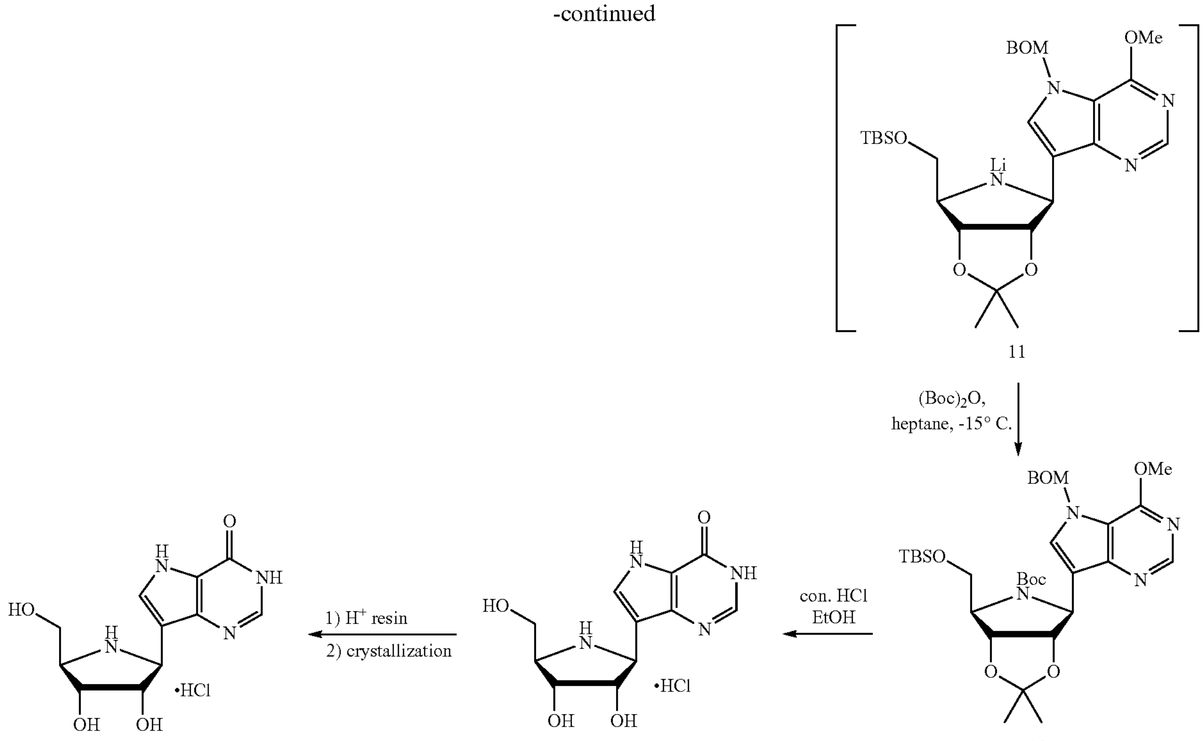

11

12 forodesine hydrochloride (1)

1

Although the above scheme has improved the method of addition and removal of BOM protecting group, n-hexyllithium is expensive and difficult to obtain; and this method still uses secondary amine (8) as raw material, and the problems, such as cumbersome preparation process, expensive cost, the unstability of imine, and being difficult to store, are still unsolved.

Therefore, for Forodesine, it is of great significance and high application value to develop a synthetic scheme with easily available raw materials, simple operation, low cost, and potential of industrialization.

Contents of the Present Invention

The object of the present invention is to provide a new method for preparing Forodesine, another object of the present invention is to provide a method for preparing Forodesine with easily available raw materials, another object of the present invention is to provide a method for preparing Forodesine with shorter reaction scheme, another object of the present invention is to provide a method for preparing Forodesine with strong operability, easy control of operation and high safety, another object of the present invention is to provide a method for preparing Forodesine with low cost, and another object of the present invention is to provide a method for preparing Forodesine suitable for scale-up production.

For achieving the above objects, the present invention provides a method for preparing a compound represented by Formula I, comprising:

treating a compound represented by Formula VII with an acid (e.g., concentrated hydrochloric acid) to generate the compound represented by Formula I;

I

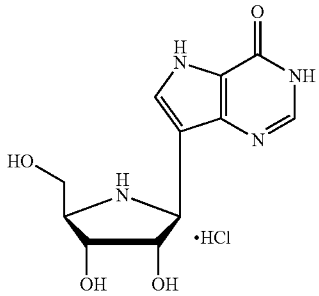

VII

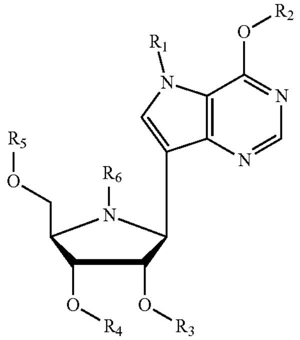

wherein:

$R_1$ is an amino protecting group, such as carbobenzoxy (Cbz), tert-butoxycarbonyl (Boc), methoxycarbonyl, ethoxycarbonyl, phthaloyl (Pht), 2,4-dimethoxybenzyl (DMB), benzyl (Bn), benzyloxymethyl (BOM);

$R_2$ is methyl or ethyl;

$R_3$, $R_4$, $R_5$ are each independently a hydroxyl protecting group, such as trimethylsilyl (TMS), tert-butyldimethylsilyl (TBDMS), benzyl (Bn), p-methoxybenzyl (PMB), 2-tetrahydropyranyl (THP), methoxymethyl (MOM), 1-ethoxyethyl (EE);

$R_6$ is an amino protecting group, such as carbobenzoxy (Cbz), tert-butoxycarbonyl (Boc), methoxycarbonyl, ethoxycarbonyl, phthaloyl (Pht), 2,4-dimethoxybenzyl (DMB), benzyl (Bn), benzyloxymethyl (BOM).

In some embodiments, in the method for preparing the compound represented by Formula I of the present invention, the compound represented by Formula VII is treated with concentrated hydrochloric acid.

In some embodiments, in the method for preparing the compound represented by Formula I of the present invention, the compound represented by Formula VII is treated with an acid under heating and refluxing conditions.

In some embodiments, in the method for preparing the compound represented by Formula I of the present invention, the compound represented by Formula VII is treated with an acid under refluxing conditions for 20 to 100 hours, such as 24 to 96 hours, 36 to 84 hours, 48 to 72 hours.

In some embodiments, in the method for preparing the compound represented by Formula I of the present invention, the compound represented by Formula VII is treated with an acid by a method comprising the following operations:

a) dissolving the compound represented by Formula VII in a first solvent to obtain a solution containing the compound represented by Formula VII;
b) adding the acid (e.g., concentrated hydrochloric acid) to the solution containing the compound represented by Formula VII, heating and refluxing.

In some embodiments, the first solvent of the present invention is tetrahydrofuran or methanol.

In some embodiments, the first solvent of the present invention is tetrahydrofuran.

In some embodiments, the method for preparing the compound represented by Formula I of the present invention further comprises:

i) removing the first solvent, adding ethanol to the obtained product, separating out and collecting a solid;
ii) optionally, purifying the obtained solid.

In some embodiments, in the method for preparing the compound represented by Formula I of the present invention, the method for purifying the obtained solid comprises:

iii) dissolving the obtained solid in water to obtain an aqueous solution;
iv) contacting the aqueous solution with a cation exchange resin, eluting with dilute hydrochloric acid (e.g., 2-4M hydrochloric acid), and collecting an eluate;
v) removing the solvent in the eluate, dissolving the product in dilute hydrochloric acid (e.g., 0.5-1.5M hydrochloric acid), heating to 40-60° C. (e.g., 45-55° C.), and cooling to room temperature;
vi) adding ethanol to the product obtained in v), stirring at room temperature for 6-10 hours, and precipitating a solid;
vii) cooling to 0° C. and standing;
viii) collecting a solid.

In some embodiments, in the compound represented by Formula VII of the present invention, $R_1$ is 2,4-dimethoxybenzyl (DMB), benzyl (Bn) or benzyloxymethyl (BOM).

In some embodiments, in the compound represented by Formula VII of the present invention, $R_1$ is 2,4-dimethoxybenzyl (DMB).

In some embodiments, in the compound represented by Formula VII of the present invention, $R_1$ is benzyl (Bn).

In some embodiments, in the compound represented by Formula VII of the present invention, $R_1$ is carbobenzoxy (Cbz).

In some embodiments, in the compound represented by Formula VII of the present invention, $R_1$ is tert-butoxycarbonyl (Boc).

In some embodiments, in the compound represented by Formula VII of the present invention, $R_1$ is methoxycarbonyl.

In some embodiments, in the compound represented by Formula VII of the present invention, $R_1$ is ethoxycarbonyl.

In some embodiments, in the compound represented by Formula VII of the present invention, $R_1$ is phthaloyl (Pht).

In some embodiments, in the compound represented by Formula VII of the present invention, $R_2$ is methyl.

In some embodiments, in the compound represented by Formula VII of the present invention, $R_3$, $R_4$, and $R_5$ are each independently benzyl (Bn), p-methoxybenzyl (PMB), methoxymethyl (MOM) or 1-ethoxyethyl (EE).

In some embodiments, in the compound represented by Formula VII of the present invention, $R_3$, $R_4$, and $R_5$ are each independently p-methoxybenzyl (PMB).

In some embodiments, in the compound represented by Formula VII of the present invention, $R_3$, $R_4$, and $R_5$ are each independently methoxymethyl (MOM).

In some embodiments, in the compound represented by Formula VII of the present invention, $R_3$, $R_4$, and $R_5$ are each independently 1-ethoxyethyl (EE).

In some embodiments, in the compound represented by Formula VII of the present invention, $R_3$, $R_4$, and $R_5$ are each independently trimethylsilyl (TMS).

In some embodiments, in the compound represented by Formula VII of the present invention, $R_3$, $R_4$, and $R_5$ are each independently tert-butyldimethylsilyl (TBDMS).

In some embodiments, in the compound represented by Formula VII of the present invention, $R_3$, $R_4$, and $R_5$ are each independently 2-tetrahydropyranyl (THP).

In some embodiments, in the compound represented by Formula VII of the present invention, $R_6$ is carbobenzoxy (Cbz), tert-butoxycarbonyl (Boc), methoxycarbonyl or ethoxycarbonyl. In some embodiments, in the compound represented by Formula VII of the present invention, $R_6$ is carbobenzoxy (Cbz).

In some embodiments, in the compound represented by Formula VII of the present invention, $R_6$ is methoxycarbonyl.

In some embodiments, in the compound represented by Formula VII of the present invention, $R_6$ is ethoxycarbonyl.

In some embodiments, in the compound represented by Formula VII of the present invention, $R_6$ is phthaloyl (Pht).

In some embodiments, in the compound represented by Formula VII of the present invention, $R_6$ is 2,4-dimethoxybenzyl (DMB).

In some embodiments, in the compound represented by Formula VII of the present invention, $R_6$ is benzyl (Bn).

In some embodiments, in the compound represented by Formula VII of the present invention, $R_6$ is benzyloxymethyl (BOM).

In some embodiments, in the compound represented by Formula VII of the present invention, $R_1$ is benzyloxymethyl (BOM).

In some embodiments, in the compound represented by Formula VII of the present invention, $R_2$ is ethyl.

In some embodiments, in the compound represented by Formula VII of the present invention, $R_3$, $R_4$, and $R_5$ are each independently benzyl (Bn).

In some embodiments, in the compound represented by Formula VII of the present invention, $R_6$ is tert-butoxycarbonyl (Boc).

In some embodiments, in the compound represented by Formula VII of the present invention, $R_1$ is benzyloxymethyl (BOM), $R_2$ is methyl, $R_3$, $R_4$, $R_5$ are each independently benzyl (Bn), $R_6$ is tert-butoxycarbonyl (Boc).

In some embodiments, the method for preparing the compound represented by Formula I of the present invention further comprises preparing a compound represented by Formula VII, which comprises:

VI

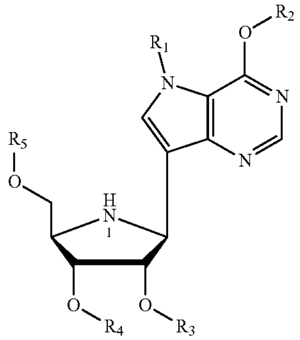

introducing an amino protecting group $R_6$ to the position 1 of a compound represented by Formula VI, wherein the definitions of $R_1$, $R_1$, $R_3$, $R_4$, $R_5$ and $R_6$ are the same as those of Formula VII.

The compound represented by Formula VI is easily oxidized, and an amino protecting group is introduced into the compound represented by Formula VI to obtain a compound represented by Formula VII with stable properties, which is convenient for subsequent separation and purification.

In some embodiments, in the compound represented by Formula VII, $R_6$ is tert-butoxycarbonyl (Boc), and the definitions of $R_1$, $R_2$, $R_3$, $R_4$, and $R_5$ are as described in the present invention, which is obtained by protection of the compound represented by Formula VI with Boc. Preferably, the compound represented by Formula VI reacts with Boc anhydride under basic conditions to obtain the compound represented by Formula VII. More preferably, the compound represented by Formula VI reacts with Boc anhydride in the presence of sodium hydroxide to obtain the compound represented by Formula VII.

In some embodiments, the method for preparing the compound represented by Formula I of the present invention further comprises preparing the compound represented by Formula VI, which comprises:

V

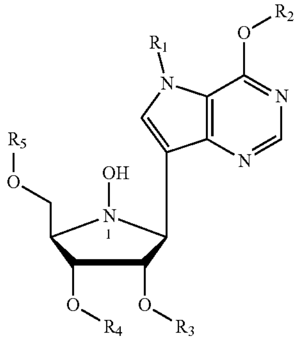

reducing a compound represented by Formula V, wherein the definitions of $R_1$, $R_1$, $R_3$, $R_4$ and $R_5$ are the same as those of Formula VII.

In some embodiments, in the method for preparing the compound represented by Formula I of the present invention, the compound represented by Formula V is reduced with a reducing agent.

In some embodiments, in the method for preparing the compound represented by Formula I of the present invention, the compound represented by Formula V is reduced with a reducing agent in a second solvent.

In some embodiments, the reducing agent of the present invention is zinc powder, iron powder or indium powder.

In some embodiments, the reducing agent of the present invention is zinc powder.

In some embodiments, the reducing agent of the present invention is iron powder.

In some embodiments, the reducing agent of the present invention is indium powder.

In some embodiments, the second solvent of the present invention is a mixed solvent of acetic acid and methanol, trifluoroacetic acid (TFA), 4-8M (e.g., 6M) hydrochloric acid, or a saturated aqueous solution of $NH_4Cl$.

In some embodiments, the second solvent of the present invention is a mixed solvent of acetic acid and methanol, preferably a mixed solvent of acetic acid and methanol with a volume ratio of 1: 3-8, for example, a mixed solvent of acetic acid and methanol with a volume ratio of 1: 4-6, such as a mixed solvent of acetic acid and methanol with a volume ratio of 1:5.

In some embodiments, the second solvent of the present invention is trifluoroacetic acid (TFA), 4-8M (e.g., 6M) hydrochloric acid, or a saturated aqueous solution of $NH_4Cl$.

In some embodiments, the second solvent of the present invention is trifluoroacetic acid (TFA).

In some embodiments, the second solvent of the present invention is 4-8M (e.g., 6M) hydrochloric acid.

In some embodiments, the second solvent of the present invention is a saturated aqueous solution of $NH_4Cl$.

In some embodiments, in the method for preparing the compound represented by Formula I of the present invention, the molar ratio of the reducing agent to the compound represented by Formula V is 15-25:1, such as 18-22:1, 20:1.

In some embodiments, the method for preparing the compound represented by Formula I of the present invention further comprises a method for preparing the compound represented by Formula V, which comprises:

II

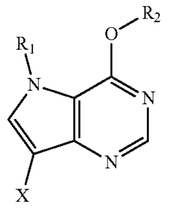

II

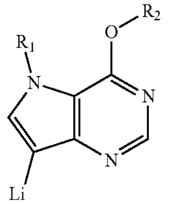

IV

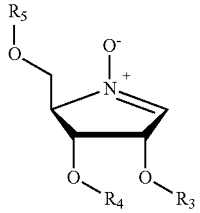

a) treating a compound represented by Formula II with a metal lithium reagent to generate a compound represented by Formula III;

b) reacting the compound represented by Formula III with a compound represented by Formula IV to generate the compound represented by Formula V, wherein the definitions of $R_1$, $R_1$, $R_3$, $R_4$, and $R_5$ are the same as those of Formula VII, and X is halogen, preferably bromine atom and iodine atom, such as bromine atom.

The compound represented by Formula III reacts with the compound represented by Formula IV to produce a pair of isomers with a diastereoselectivity of 7:1, wherein the main product is the compound represented by Formula V. The compound represented by Formula V is reduced to the compound represented by Formula VI, and the intermediate is easily oxidized. An amino protecting group is introduced into the compound represented by the Formula VI to obtain the compound of the Formula VII with stable properties, so that the diastereomers generated in the above reaction process can be easily separated.

In some embodiments, the metal lithium reagent of the present invention is n-butyllithium, tert-butyllithium, phenyllithium, and sec-butyllithium.

In some embodiments, the metal lithium reagent of the present invention is n-butyllithium.

In some embodiments, the metal lithium reagent of the present invention is tert-butyllithium.

In some embodiments, the metal lithium reagent of the present invention is phenyllithium.

In some embodiments, the metal lithium reagent of the present invention is sec-butyllithium.

In some embodiments, in the method for preparing the compound represented by Formula I of the present invention, the compound represented by Formula II is treated with the metal lithium reagent in a third solvent.

In some embodiments, the third solvent of the present invention is methyl tert-butyl ether, tetrahydrofuran (THF), anisole, n-hexane or toluene.

In some embodiments, the third solvent of the present invention is methyl tert-butyl ether.

In some embodiments, the third solvent of the present invention is anhydrous methyl tert-butyl ether.

In some embodiments, the third solvent of the present invention is tetrahydrofuran (THF).

In some embodiments, the third solvent of the present invention is anisole.

In some embodiments, the third solvent of the present invention is n-hexane.

In some embodiments, the third solvent of the present invention is toluene.

In some embodiments, in the method for preparing the compound represented by Formula I according to the present invention, the compound represented by Formula II is treated with the metal lithium reagent under the conditions of −60° C. to 0° C. (e.g., −40° C., −20° C.).

In some embodiments, in the method for preparing the compound represented by Formula I according to the present invention, the compound represented by Formula II is treated with the metal lithium reagent under the conditions of −40° C. to 0° C.

In some embodiments, in the method for preparing the compound represented by Formula I according to the present invention, the compound represented by Formula II is treated with the metal lithium reagent under the conditions of −60° C. to −20° C.

In some embodiments, in the method for preparing the compound represented by Formula I according to the present invention, the compound represented by Formula II is treated with the metal lithium reagent under the conditions of −40° C. to −20° C.

In some embodiments, in the method for preparing the compound represented by Formula I according to the present invention, the molar ratio of the metal lithium reagent to the compound represented by Formula II is 1-1.5:1, for example, 1.2:1.

In some embodiments, in the method for preparing the compound represented by Formula I according to the present invention, the compound represented by Formula III reacts with the compound represented by Formula IV in a third solvent.

In some embodiments, in the method for preparing compound represented by Formula I according to the present invention, the feed molar ratio of the compound represented by Formula II to the compound represented by Formula IV is 1.4-2.2:1, such as 1.6-2:1, for example 1.8:1.

In some embodiments, in the method for preparing the compound represented by Formula I according to the present invention, the compound represented by Formula III reacts with the compound represented by Formula IV under the conditions of −60° C. to 0° C. (e.g., −40° C., −20° C.).

In some embodiments, in the method for preparing the compound represented by Formula I according to the present invention, the compound represented by Formula III reacts with the compound represented by Formula IV under the conditions of −40° C. to 0° C.

In some embodiments, in the method for preparing the compound represented by Formula I according to the present invention, the compound represented by Formula III reacts with the compound represented by Formula IV under the conditions of −60° C. to −20° C.

In some embodiments, in the method for preparing the compound represented by Formula I according to the present invention, the compound represented by Formula III reacts with the compound represented by Formula IV under the conditions of −40° C. to −20° C.

The present invention further provides an intermediate compound represented by Formula V, Formula VI or Formula VII,

V

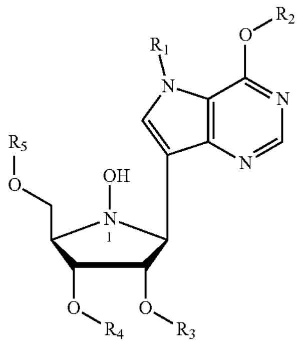

VI

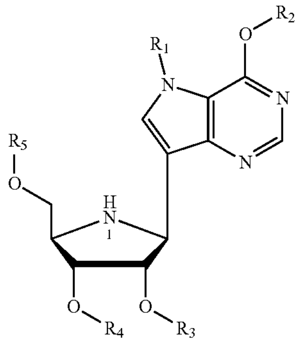

VII

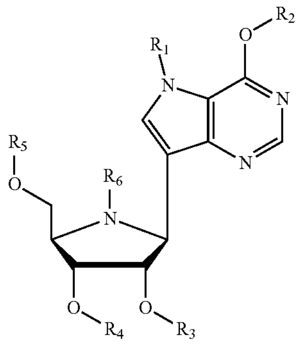

wherein, the definitions of $R_1$, $R_1$, $R_3$, $R_4$, $R_5$, and $R_6$ are the same as those of Formula VII.

In some embodiments, the intermediate compound is selected from the group consisting of:

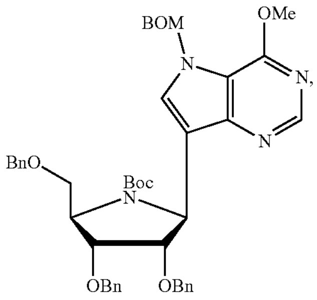

-continued

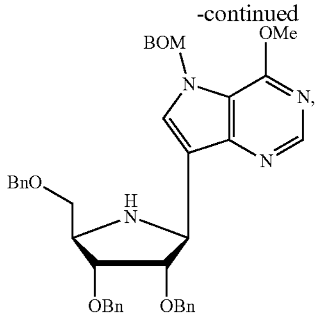

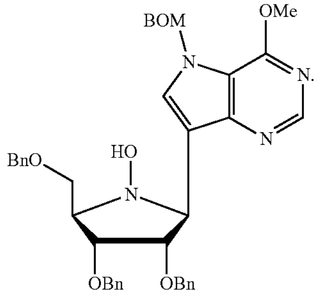

The present invention further provides a method for preparing Forodesine or a salt thereof, comprising:

a) preparing the compound represented by Formula I by using the method of the present invention;

b) converting the compound represented by Formula I into a free form of Forodesine, or converting the compound represented by Formula I into a desired salt of Forodesine.

In the present invention, the compound represented by Formula IV is a nitrone compound, for example, a nitrone compound represented by Formula IV in which $R_3$, $R_4$, $R_5$ are each independently of benzyl (Bn), which can be prepared by referring to a method in literature (Tetrahedron, 2009, 65, 93-100). The compound represented by Formula II in which $R_1$ is benzyloxymethyl (BOM), $R_2$ is methyl, and X is a bromine atom can be prepared by referring to a method in literature (Journal of Organic Chemistry, 2001, 66(17), 5723-5730).

Definitions

Unless otherwise defined below, all technical and scientific terms used herein are intended to have the same meaning as commonly understood by one skilled in the art. References to techniques used herein are intended to refer to techniques commonly understood in the art, including those variations or substitutions of equivalent techniques that would be obvious to one skilled in the art. While the following terms are believed to be well understood by one skilled in the art, the following definitions are set forth to better explain the present invention.

As used herein, the terms “comprising”, “including”, “having”, “containing” or “involving” and other variations thereof herein are inclusive or open-ended and do not exclude other unenumerated elements or method steps.

As used herein, the term “halogen” group is defined to include F, Cl, Br or I.

As used herein, the term “concentrated hydrochloric acid” generally refers to hydrochloric acid with a mass fraction of 36% to 38%, and a substance concentration of 12 mol/L.

As used herein, the term “dilute hydrochloric acid” refers to hydrochloric acid with a mass fraction of less than 20%.

Unless otherwise apparent from the context, all numerical values provided herein are modified by the term “about”, that is, the numerical values disclosed herein include not only the numerical value itself, but also the numerical values modified by "about". For the specific values as used herein, the term "about" should be understood as within a range of normal tolerance in the art, for example, within ±10%, ±9%, ±8%, ±7%, ±6%, ±5%, ±4%, ±3%, ±2%, ±1%, ±0.5%, ±0.1%, ±0.05% or ±0.01%.

Beneficial effects of the present invention:

The method for preparing the compound Forodesine hydrochloride represented by Formula I provided by the present invention has one or more of the following advantages:

1) the raw materials and solvents used in this method are cheap and easy to be obtained;
2) the method uses a nitrone compound as a raw material this raw material is stable and easy to be stored, easy to prepare on a large scale, simple and convenient to prepare, in which the reagents and solvents involved are cheap and easy to be obtained, and the operation is simple;
3) the synthesis process of this method is easy to operate, the synthesis scheme is short, and the overall yield is high, for example about 30%;
4) the production cost of this method is low;
5) the Forodesine hydrochloride prepared by this method has high purity, and the purity can reach more than 99.8%, such as 99.9%.
6) the method is suitable for industrial production.

Peak information (wavelength: 254 nm):

| Peak # | RetTime [min] | Width [min] | Area [mAU*s] | Height [mAU] | Area % |
|---|---|---|---|---|---|
| 1 | 7.383 | 0.2606 | 19.30883 | 1.03992 | 0.0130 |
| 2 | 9.307 | 0.2463 | 105.91992 | 6.42738 | 0.0714 |
| 3 | 10.550 | 0.7339 | 1.48284e5 | 3111.81201 | 99.9156 |

SPECIFIC MODELS FOR CARRYING OUT THE PRESENT INVENTION

In order to further illustrate the technical effect of the present invention, the present invention will be described in detail below through examples. The examples provided are merely to illustrate the method of the present invention and are not intended to limit the present invention in any way.

Unless otherwise specified, the reagents, methods and equipment used in the present invention are conventional reagents, methods and equipment in the art.

Example: Preparation of Forodesine Hydrochloride

The compound represented by Formula 1 of the example of the present invention, i.e., Forodesine hydrochloride, was prepared by the synthetic scheme as follows:

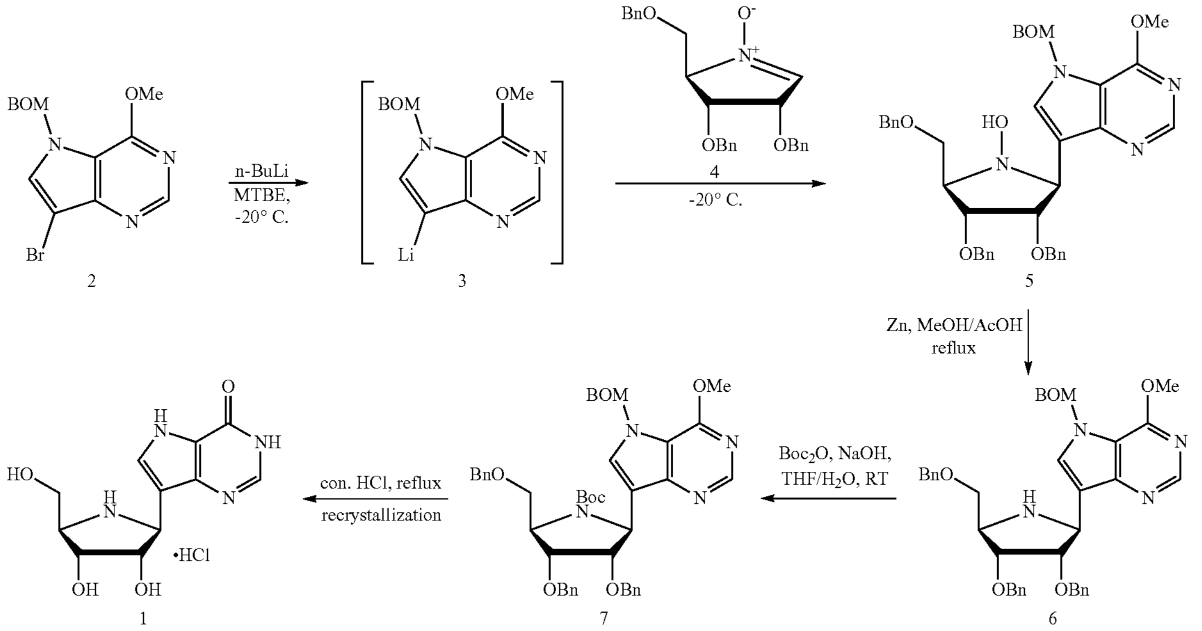

Figure 1:
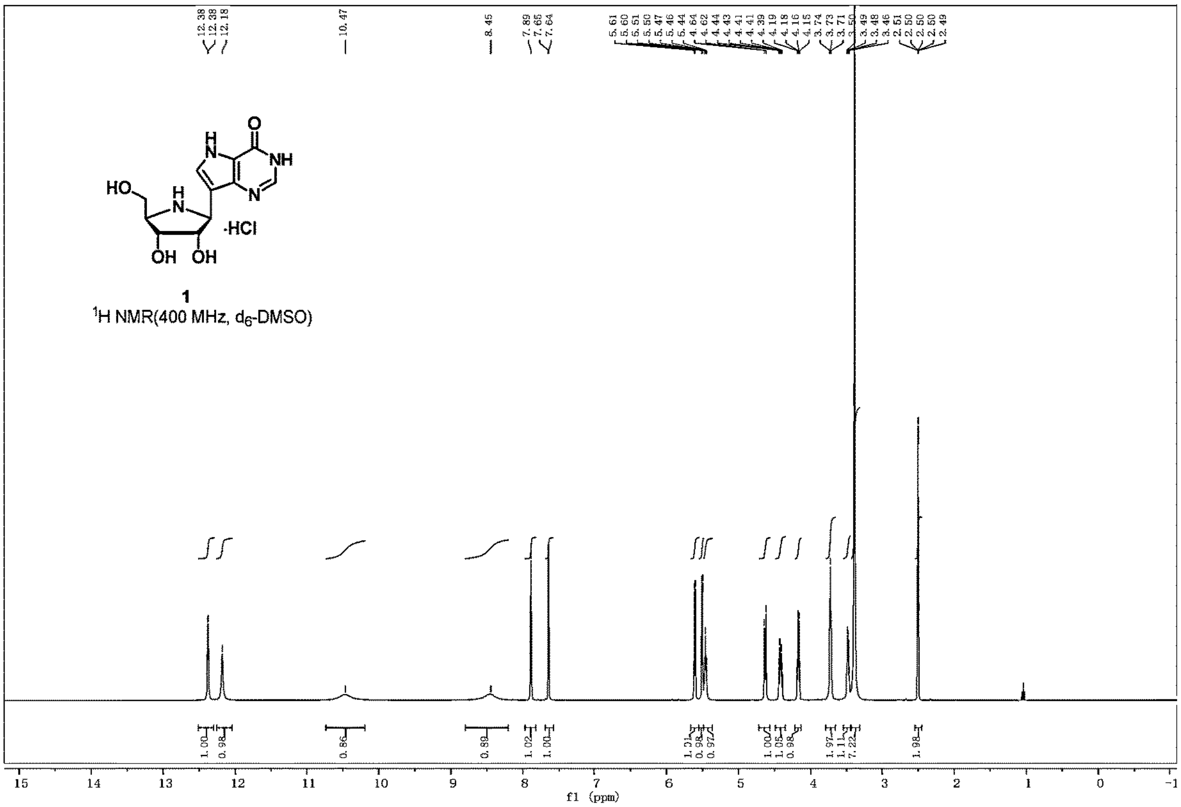
FIG. 1 shows the $^1$H-NMR nuclear magnetic spectrum of Forodesine hydrochloride of the present invention.

column: Agilent ZORBAX SB-C18, 4.6×150 mm, 5 μm;

solvent: 0.1% TFA/$H_2O$=100%; flow: 0.3 mL/min;

1) Preparation of Compound 5:

The bromopurine derivative (2) (22.5 g, 64.7 mmol) was dissolved in anhydrous methyl tert-butyl ether (600 mL), cooled to −20° C., and n-butyllithium (2.5M, 31 mL, 78 mmol) was slowly added dropwise. After the completion of the dropwise addition, the mixture was stirred at −20° C. for 1 hour, then warmed to room temperature and stirred for 10 minutes, and then cooled to −20° C., then a nitrone (4) (15.0 g, 35.9 mmol) in methyl tert-butyl ether (50 mL) was slowly added dropwise, the resultant mixture reacted at −20° C. for 15 hours, a saturated ammonium chloride solution was added to quench the reaction. the resultant mixture was warmed to room temperature, ethyl acetate was added for dilution, the organic layer and the aqueous layer were separated, the aqueous layer was extracted three times with ethyl acetate, the organic layers were combined, dried over anhydrous sodium sulfate, and the solvent was removed under reduced pressure to obtain a crude product of hydroxylamine (5), which was directly used in the next step without separation and purification.

2) Preparation of Compound 6:

The crude hydroxylamine (5) obtained in the previous step was dissolved in a mixed solvent of acetic acid and methanol (V/V=1:5, 60 mL), zinc powder (47.0 g, 0.72 mol) was added, and the mixture was heated to reflux for 2 hours. Then the reaction solution was cooled to room temperature, filtered through diatomite to remove an insoluble substance, the filtrate was concentrated and drained to obtain a crude secondary amine (6), which was directly used in the next step without separation and purification.

3) Preparation of Compound 7:

The crude secondary amine (6) obtained in the previous step was dissolved in tetrahydrofuran (150 mL), 3M aqueous sodium hydroxide solution (150 mL, 0.45 mol) was added, the pH value of the solution was adjusted to 10, and BOC anhydride (15.7 g, 71.8 mmol) was added, and the resultant reaction solution reacted at room temperature for 15 hours. After monitoring the completion of the reaction by LC-MS, the reaction solution was filtered through diatomite to remove an insoluble substance. The tetrahydrofuran in the filtrate was removed under reduced pressure, the residue was diluted with ethyl acetate, and an organic layer and an aqueous layer were separated, the aqueous layer was extracted three times with ethyl acetate, and then the organic layers were combined, dried over anhydrous sodium sulfate, the solvent was removed under reduced pressure, and the crude product was separated and purified through silica gel column chromatography (petroleum ether:ethyl acetate (V/V)=5:1) obtain a light yellow oil (7) (11.0 g, 40%). LC-MS m/z for $C_{46}H_{51}N_4O_7$ $[M+H]^+$ calculated 771.4; found 771.4

4) Preparation of Forodesine Hydrochloride

Compound 7 (11.0 g) was dissolved in tetrahydrofuran (50 mL), concentrated hydrochloric acid (12M (36° ~38%), 100 mL) was added, the resultant mixture was heated to reflux for 72 hours, concentrated to dryness, and filtered, the solvent in the filtrate was removed under reduced pressure, a brown-red solid was obtained, to which ethanol (50 mL) was added, the resultant mixture was ground, filtered, and the solid was collected to obtain crude Forodesine hydrochloride (1) with a yield of about 78%.

5) Purification and Refinement of Forodesine Hydrochloride

Figure 2:
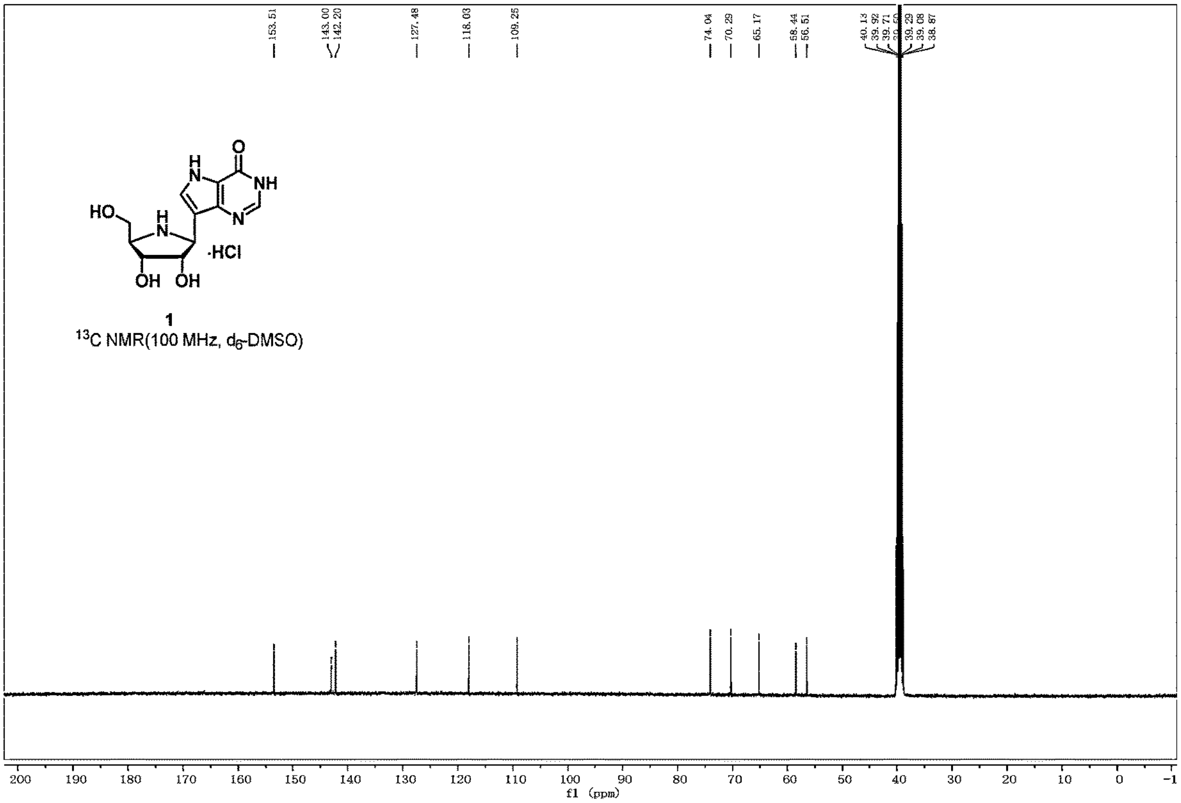
FIG. 2 shows the $^{13}$C-NMR nuclear magnetic spectrum of Forodesine hydrochloride of the present invention.
Figure 3:
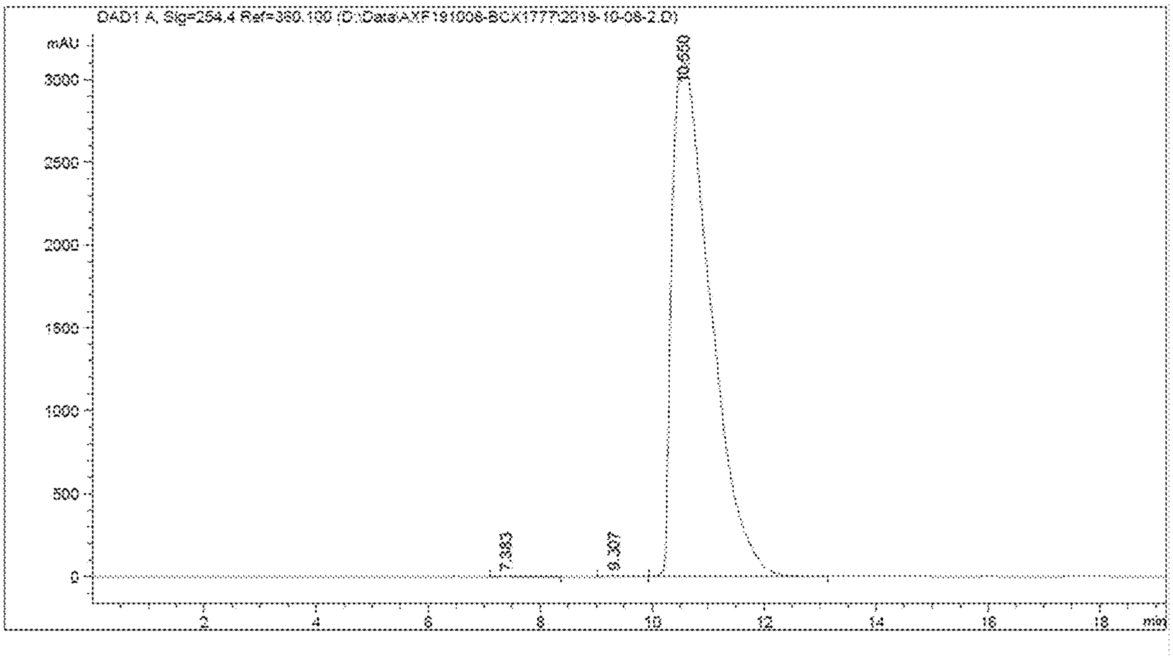
FIG. 3 shows the HPLC spectrogram of Forodesine hydrochloride of the present invention.

The solid Forodesine hydrochloride was dissolved in water, the resultant mixture was filtered through a cation exchange resin (eluted with 5L of 3M dilute hydrochloric acid), the hydrochloric acid eluate was collected, concentrated to dryness, the residue was dissolved in 1M dilute hydrochloric acid, heated to 50° C., then cooled to room temperature, ethanol was slowly added until a solid was precipitated. The resultant mixture was stirred at 20° C. for 8 hours, then was cooled to 0° C. and stood for 2 hours. A solid was collected through filtration, and dried to obtain a white solid Forodesine hydrochloride (about 3.0 g), and its structure and purity identification results were shown in FIGS. 1 to 3, and its purity was about 99.9%.

The overall yield of this example was about 30%.

$^1H$ NMR (400 MHz, CD3SOCD3) δ12.38 (s, 1H), 12.18 (s, 1H), 10.47 (s, 1H), 8.45 (s, 1H), 7.89 (s, 1H), 7.65 (d, J=4.0 Hz, 1H), 5.60 (d, J=4.0 Hz, 1H), 5.50 (d, J=4.0 Hz, 1H), 5.46 (t, J=4.0 Hz, 1H), 4.63 (d, J=8.0 Hz, 1H), 4.44-4.39 (m, 1H), 4.19— 4.15 (m, 1H), 3.74— 3.71 (m, 1H), 3.50-3.46 (m, 1H). $^{13}C$ NMR (100 MHz, $CD_3SOCD_3$) δ153.5, 143.0, 142.2, 127.5, 118.0, 109.2, 74.0, 70.3, 65.2, 58.4, 56.5. LC-MS m/z for $C_{11}H_{15}N_4O_4[M+H]^+$ calculated 267.1; found 267.1.

Finally, it should be noted that the above examples are only used to illustrate the technical solution of the present invention and not to limit it. Although the technical solution of the present invention has been described in detail with reference to the preferred examples, one skilled in the art should understand that the technical solution of the present invention can be modified or equivalently replaced without departing from the spirit and scope of the present invention, all of these changes should be included in the protection scope of the present invention.

What is claimed is:

1. A method for preparing a compound represented by Formula I, comprising:

II

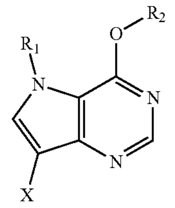

II

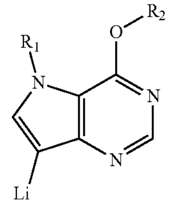

IV

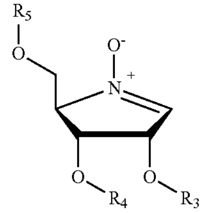

a) treating a compound represented by Formula II with a metal lithium reagent to generate a compound represented by Formula III;

b) reacting the compound represented by Formula III with a compound represented by Formula IV to generate a compound represented by Formula V;

V

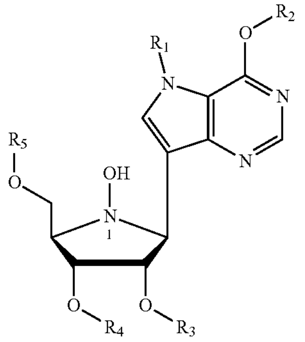

VI

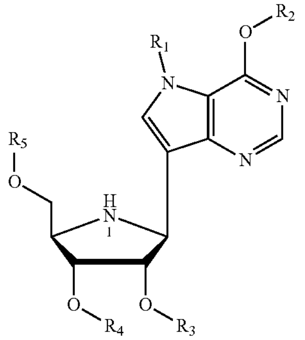

reducing the compound represented by Formula V to generate a compound represented by Formula VI;

introducing an amino protecting group $R_6$ into the position 1 of the compound represented by Formula VI to generate a compound represented by Formula VII;

treating the compound represented by Formula VII with an acid to generate the compound represented by Formula I;

VII

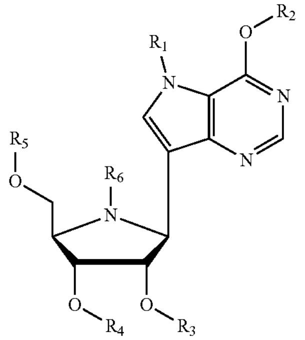

I

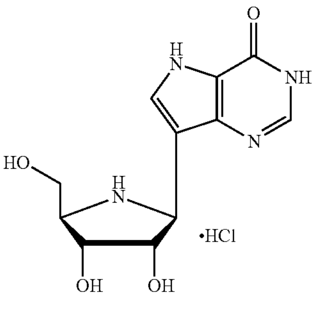

wherein:

X is halogen;

$R_1$ is an amino protecting group selected from the group consisting of carbobenzoxy (Cbz), tert-butoxycarbonyl (Boc), methoxycarbonyl, ethoxycarbonyl, phthaloyl (Pht), 2,4-dimethoxybenzyl (DMB), benzyl (Bn), and benzyloxymethyl (BOM);

$R_2$ is methyl or ethyl;

$R_3$, $R_4$, $R_5$ are each independently a hydroxyl protecting group selected from the group consisting of trimethylsilyl (TMS), tert-butyldimethylsilyl (TBDMS), benzyl (Bn), p-methoxybenzyl (PMB), 2-tetrahydropyranyl (THP), methoxymethyl (MOM), and 1-ethoxyethyl (EE);

$R_6$ is an amino protecting group selected from the group consisting of carbobenzoxy (Cbz), tert-butoxycarbonyl (Boc), methoxycarbonyl, ethoxycarbonyl, phthaloyl (Pht), 2,4-dimethoxybenzyl (DMB), benzyl (Bn), and benzyloxymethyl (BOM).

2. The method according to claim 1, wherein the acid is concentrated hydrochloric acid.

3. The method according to claim 1, wherein the compound represented by the Formula VII is treated with the acid under heating and refluxing conditions.

4. The method according to claim 3, wherein the compound represented by Formula VII is treated with the acid under refluxing conditions for 20 to 100 hours.

5. The method according to claim 1, wherein the compound represented by Formula VII is treated with the acid by a method comprising the following operations:

a) dissolving the compound represented by Formula VII in a first solvent to obtain a solution containing the compound represented by Formula VII;

b) adding the acid to the solution containing the compound represented by Formula VII, heating and refluxing.

6. The method according to claim 5, wherein the method further comprises:

i) removing the first solvent, adding ethanol to the obtained product, separating out and collecting a solid;

ii) optionally, purifying the obtained solid.

7. The method according to claim 1, characterized by one or more of the following items:

(a) $R_1$ is 2,4-dimethoxybenzyl (DMB), benzyl (Bn) or benzyloxymethyl (BOM);

(b) $R_2$ is methyl;

(c) $R_3$, $R_4$, $R_5$ are each independently benzyl (Bn), p-methoxybenzyl (PMB), methoxymethyl (MOM) or 1-ethoxyethyl (EE);

(d) $R_6$ is carbobenzoxy (Cbz), tert-butoxycarbonyl (Boc), methoxycarbonyl or ethoxycarbonyl.

8. The method according to claim 7, characterized by one or more of the following items:

(a) $R_1$ is benzyloxymethyl (BOM);

(b) $R_2$ is methyl;

(c) $R_3$, $R_4$, $R_5$ are each independently benzyl (Bn);

(d) $R_6$ is tert-butoxycarbonyl (Boc).

9. A method for preparing Forodesine or salt thereof, comprising:

a) preparing the compound represented by Formula I by using the method according to claim 1;

b) converting the compound represented by Formula I into a free form of Forodesine, or converting the compound represented by Formula I into a desired salt of Forodesine.

10. The method according to claim 4, wherein the compound represented by Formula VII is treated with the acid under refluxing conditions for 24 to 96 hours.

11. The method according to claim 5, wherein the first solvent is tetrahydrofuran or methanol.

12. The method according to claim 6, wherein the obtained solid is purified by a method comprising:

iii) dissolving the obtained solid in water to obtain an aqueous solution;

iv) contacting the aqueous solution with a cation exchange resin, eluting with dilute hydrochloric acid, and collecting an eluate;

v) removing the solvent in the eluate, dissolving the product in dilute hydrochloric acid, heating to 40-60° C., and cooling to room temperature;

vi) adding ethanol to the product obtained in v), stirring at room temperature for 6-10 hours, and precipitating out a solid;

vii) cooling to 0° C. and standing;

viii) collecting a solid.

13. The method according to claim 12, characterized by one or more of the following items:

(a) the dilute hydrochloric acid in iv) is 2-4M hydrochloric acid;

(b) the dilute hydrochloric acid in v) is 0.5-1.5M hydrochloric acid;

(c) the step v) comprises removing the solvent in the eluate, dissolving the product in dilute hydrochloric acid, heating to 45-55° C., and cooling to room temperature.

14. The method according to claim 1, characterized by one or more of the following items:

(a) the compound represented by Formula V is reduced with a reducing agent;

(b) the compound represented by Formula V is reduced with a reducing agent in a second solvent;

(c) the molar ratio of the reducing agent to the compound represented by Formula Vis 15-25:1.

15. The method according to claim 14, characterized by one or more of the following items:

(a) the reducing agent is zinc powder, iron powder or indium powder;

(b) the second solvent is a mixed solvent of acetic acid and methanol, trifluoroacetic acid (TFA), 4-8M hydrochloric acid, or saturated aqueous solution of $NH_4Cl$;

(c) the molar ratio of the reducing agent to the compound represented by Formula Vis 18-22:1.

16. The method according to claim 15, characterized by one or more of the following items:

(a) the reducing agent is zinc powder;

(b) the second solvent is a mixed solvent of acetic acid and methanol, and the mixed solvent of acetic acid and methanol is a mixed solvent of acetic acid and methanol with a volume ratio of 1:3-8.

17. The method according to claim 1, characterized by one or more of the following items:

(a) The metal lithium reagent is n-butyllithium, tert-butyllithium, phenyllithium, or sec-butyllithium;

(b) X is bromine atom and iodine atom;

(c) the compound represented by Formula II is treated with the metal lithium reagent in a third solvent;

(d) the compound represented by the Formula II is treated with the metal lithium reagent under the conditions of −60° C. to 0° C.;

(e) the molar ratio of the metal lithium reagent to the compound represented by Formula II is 1-1.5:1;

(f) the compound represented by the Formula III reacts with the compound represented by the Formula IV in a third solvent;

(g) the feed molar ratio of the compound represented by Formula II to the compound represented by Formula IV is 1.4-2.2:1;

(h) the compound represented by the Formula III reacts with the compound represented by the Formula IV under the conditions of −60° C. to 0° C.

18. The method according to claim 17, characterized by one or more of the following items:

(a) The metal lithium reagent is n-butyllithium;

(b) X is bromine atom;

(c) the third solvent is methyl tert-butyl ether, tetrahydrofuran (THF), anisole, n-hexane or toluene;

(d) the compound represented by the Formula II is treated with the metal lithium reagent under the conditions of −40° C. or −20° C.;

(e) the molar ratio of the metal lithium reagent to the compound represented by Formula II is 1.2:1;

(f) the feed molar ratio of the compound represented by Formula II to the compound represented by Formula IV is 1.6-2:1;

(g) the compound represented by the Formula III reacts with the compound represented by the Formula IV under the conditions of −40° C. or −20° C.

19. The method according to claim 1, wherein the compound of Formula VII is

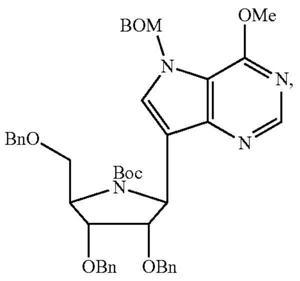

the compound of Formula VI is

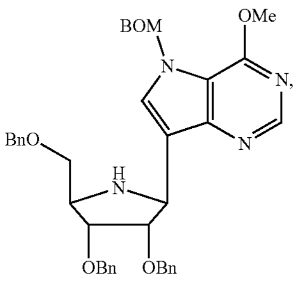

and the compound of Formula V is
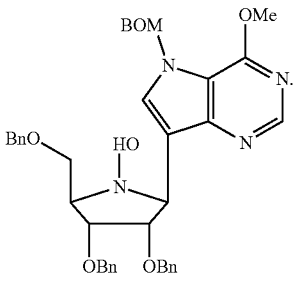
* * * * *